US009320759B2

(12) United States Patent
Pan

(10) Patent No.: US 9,320,759 B2
(45) Date of Patent: Apr. 26, 2016

(54) METHODS AND COMPOSITIONS FOR TREATING, REDUCING OR PREVENTING DETERIORATION OF THE VISUAL SYSTEM OF ANIMALS

(75) Inventor: Yuanlong Pan, Chesterfield, MO (US)

(73) Assignee: Nestec S.A, Vevey (CH)

( * ) Notice: Subject to any disclaimer, the term of this patent is extended or adjusted under 35 U.S.C. 154(b) by 315 days.

(21) Appl. No.: 13/981,220

(22) PCT Filed: Jan. 24, 2012

(86) PCT No.: PCT/US2012/022297
§ 371 (c)(1),
(2), (4) Date: Jul. 23, 2013

(87) PCT Pub. No.: WO2012/103049
PCT Pub. Date: Aug. 2, 2012

(65) Prior Publication Data
US 2013/0309329 A1 Nov. 21, 2013

Related U.S. Application Data

(60) Provisional application No. 61/461,913, filed on Jan. 25, 2011.

(51) Int. Cl.
*A61K 31/20* (2006.01)
*A61K 33/00* (2006.01)
*A61K 45/06* (2006.01)
*A61K 35/60* (2006.01)

(52) U.S. Cl.
CPC ............... *A61K 33/00* (2013.01); *A61K 31/20* (2013.01); *A61K 35/60* (2013.01); *A61K 45/06* (2013.01)

(58) Field of Classification Search
CPC .............................. A61K 33/00; A61K 31/20
USPC .......................................................... 424/718
See application file for complete search history.

(56) References Cited

U.S. PATENT DOCUMENTS

| 2005/0249821 A1 | 11/2005 | Paul |
| 2006/0046982 A1 | 3/2006 | Waugh |
| 2006/0088574 A1 | 4/2006 | Manning |
| 2009/0110674 A1* | 4/2009 | Loizou .................. A61K 36/00 424/94.2 |
| 2009/0203786 A1 | 8/2009 | Waldron et al. |
| 2009/0325999 A1 | 12/2009 | Du |
| 2010/0159029 A1 | 6/2010 | Lang |
| 2010/0233304 A1 | 9/2010 | Pan |
| 2010/0292330 A1 | 11/2010 | Pan et al. |
| 2012/0149777 A1 | 6/2012 | Larson et al. |

FOREIGN PATENT DOCUMENTS

| JP | 2009505999 A | 2/2009 |
| WO | 2007022991 A1 | 1/2007 |
| WO | 2008143642 A2 | 11/2008 |
| WO | 2009079544 A1 | 6/2009 |
| WO | 2009088433 A1 | 7/2009 |
| WO | 2010118761 A1 | 10/2010 |
| WO | 2011106482 A1 | 1/2011 |

OTHER PUBLICATIONS

McCarty M F: "Nitric Oxide Deficiency, Leukocyte Activation, and Resultant Ischemia Are Crucial to the Pathogenisis of Diabetic Retinopathy/Neuropathy:Preventive Potential of Antioxidants Essential Fatty Acids, Chromium, Ginkgolides, and Pentoxyfylline", Medical Hypotheses, Eden Press, Penrith, US vol. 50, No. 5, May 1, 1998 pp. 435-449.
George C.Y. Chiou et al: "Ocular Hypotensive Effects of L-Arginine and its Derivatives and Their Actions on Ocular Blood Flow", Journal of Occular Pharmacology and Therapeutics, vol. 11, No. 1, Jan. 1, 1995, pp. 1-10.
Mendrinos E et al: "Intravitreal I-Arginine injection reverses the retinal arteriolar vasoconstriction that occurs after experimental acute branch retinal vein occlusion", Experimental Eye Research, Academic Press Ltd., London, vol. 91, No. 2, Aug. 1, 2010, pp. 205-210.
Chiou G C Y: "Review: Effects of Nitric Oxide on Eye Diseases and Their Treatment", Journal of Ocular Pharmacology and Therapeutics, Mary Ann Liebert, Inc., New York, NY, US, vol. 17, No. 2, Apr. 1, 2001 pp. 189-198.
Connor Kip M et al: "Increased dietary intake of omega-3-polyunsaturated fatty acids reduces pathological retinal angiogenesis", Nature Medicine, Nature Publishing Group, New York, NY, US, vol. 13, No. 7, Jul. 1, 2007 pp. 868-873.
Jingsheng Tuo et al: "A High Omega-3 Fatty Acid Diet Reduces Retinal Lesions in a Murine Model of Macular Degeneration", The American Hournal of Pathology, vol. 175, No. 2, Aug. 1, 2009, pp. 799-807.
Gaby A R: "Nutritional therapies for ocular disorders: Part three", Alternative Medicine Review, Thorne Research Inc., Sandpoint, US, vol. 13, No. 3, Jan. 1, 2008, pp. 191-204.
International Search Report and Written Opinion, PCT/US2012/22297 dated May 11, 2012.
Supplemental European Search Report, Application No. 12739643.4 dated Nov. 6, 2014.

* cited by examiner

*Primary Examiner* — Kristin Vajda
(74) *Attorney, Agent, or Firm* — Ronald A. Burchett; Julie M. Lappin

(57) ABSTRACT

Methods and compositions for treating, reducing, or preventing deterioration of at least one component of the visual system of an animal are disclosed. The methods comprise administering to the animal a composition comprising UFA and NORC in an amount effective to treat, reduce, or prevent deterioration of at least one component of the visual system. Methods extending the prime years of an animal's life, improving the quality of life, and promoting health and wellness of an animal using compositions comprising UFA and NORC are also disclosed.

25 Claims, No Drawings

METHODS AND COMPOSITIONS FOR TREATING, REDUCING OR PREVENTING DETERIORATION OF THE VISUAL SYSTEM OF ANIMALS

CROSS REFERENCE TO RELATED APPLICATIONS

This application is a national stage application under 35 USC §371 of PCT/US2012/022297 filed on 24 Jan. 2012 and claims priority to U.S. Provisional Application Ser. No. 61/461,913 filed 25 Jan. 2011, the disclosure of which are incorporated herein by this reference.

BACKGROUND OF THE INVENTION

1. Field of the Invention

The invention relates generally to methods and compositions for treating, reducing, or preventing deterioration of the visual system of animals and particularly to methods and compositions using unsaturated fatty acid and nitric acid releasing compounds for treating, reducing, or preventing deterioration of the retina and optic nerve in animals.

2. Description of the Related Art

Unsaturated fatty acids and nitric oxide releasing compounds are known to be useful for enhancing cognitive function and for minimizing a decline in cerebrovascular function associated with aging, disease (such as Alzheimer's disease), and stroke.

In addition to changes in cognitive and other functions, animals often experience a loss or deterioration of visual function associated with normal (i.e., non-pathologic) aging and with various age-related diseases such as advanced macular degeneration (AMD), Alzheimer's disease (AD), glaucoma, and certain retinopathies. In particular, various components of an animal's visual system, including both the retina and the optic nerve, are subject to age-related and disease-related changes (mainly loss of cells due to hypoxia and hypoxia-induced oxidative stress) that negatively affect vision. The consequences of such visual deterioration include not only difficulties with reading or locating objects, but also problems in the perception and/or recognition of color, depth perception, distinguishing structure from motion, and the like. Similarly, a loss or deterioration of visual function can result from injury and similar causes.

In view of the foregoing, the development of methods and compositions for treating, reducing, or preventing deterioration of the visual system of an animal, particularly of the retina and optic nerve in animals, is needed.

SUMMARY OF THE INVENTION

It is, therefore, an object of the invention to provide methods for reducing, preventing, or treating at least one symptom or cause of deterioration of the visual system of an animal, including the optic nerve, retina, and other components of the visual system.

It is another object of the invention to provide methods for reducing, preventing, or treating age-related deterioration of vision in animals.

It is another object of the invention to provide methods for reducing, preventing, or treating disease-related deterioration of vision in animals.

It is a further object of the invention to provide methods for adjusting the diet of animals to reduce, prevent, or treat deterioration of visual system of the animals.

It is another object of the invention to provide methods for preserving or maintaining vision during the prime years and throughout an animal's life.

It is another object of the invention to provide methods for promoting the health or wellness of an animal by reducing, preventing, or treating deterioration of vision in animals.

One or more of these or other objects are achieved by identifying an animal susceptible to or suffering from deterioration of one or more components of the visual system and administering in conjunction to the animal one or more unsaturated fatty acids (UFA) and one or more nitric oxide releasing compounds (NORC) in an amount effective for treating, reducing, or preventing deterioration of such components of the visual system. In certain embodiments, one or more B vitamins, one or more antioxidants, or combinations thereof are administered in conjunction with the UFA and NORC in amounts effective for treating, reducing, or preventing deterioration of such components of the visual system.

Other and further objects, features, and advantages of the invention will be readily apparent to those skilled in the art.

DETAILED DESCRIPTION OF THE INVENTION

Definitions

The following abbreviations may be used herein: AA, arachidonic acid; aka, also known as; ALA, alpha-linolenic acid; ANOVA, analysis of variance; AREDS, Age-Related Eye Diseases Study; DHA, docosahexaenoic acid; DPA, docosapentaenoic acid; EPA, eicosapentaenoic acid; LA, linoleic acid; L-Arg, L-arginine; NO, nitric oxide; NORC, nitric oxide releasing compound or compounds; RNA, ribonucleic acid; RNAi, inhibitory RNA; TTC, tetrazolium chloride; TUNEL, terminal deoxynucleotidyl transferase dUTP nick end labeling; UFA, unsaturated fatty acids (as used herein UFA refers to one or more such fatty acids); and VEGF, vascular endothelial growth factor.

The term "animal" means any animal that can benefit from improvement in, or a decrease in loss of age-related or other deterioration of the animal's visual system, including human, avian, bovine, canine, equine, feline, hicrine, lupine, murine, ovine, or porcine animals, and preferably a domesticated animal, and more preferably a companion animal.

The term "companion animals" means domesticated animals such as dogs, cats, birds, rabbits, guinea pigs, ferrets, hamsters, mice, gerbils, pleasure horses, cows, goats, sheep, donkeys, pigs, and more exotic species kept by humans for company, amusement, psychological support, education, physical assistance, extrovert display, and all of the other functions that humans desire or need to share with animals of other species.

The term "individual" when referring to an animal means an individual animal of any species or kind.

The term "unsaturated fatty acid" or "UFA" means one or more polyunsaturated fatty acids and/or monounsaturated fatty acids, including monocarboxylic acids having at least one double bond. UFAs include (n-6) fatty acids such as linoleic acid (LA) and arachidonic acid (AA) and (n-3) fatty acids such as eicosapentaenoic acid (EPA), alpha-linolenic acid (ALA), docosapentaenoic acid (DPA) and docosahexaenoic acid (DHA). UFAs also include myristoleic acid, palmitoleic acid, oleic acid, linoleic acid, cis-vaccenic acid, and erucic acid.

The term "fish oil" means a fatty or oily extract, relatively rich in UFA, whether crude or purified, obtained from a sea animal, preferably a cold-water fish such as, but not limited to, salmon, tuna, mackerel, menhaden, herring, sea bass, striped bass, pollock, flounder, halibut, catfish, lake trout, anchovies, and sardines, as well as shark, swordfish, tilefish, shrimp, and clams, or any combination thereof. Fish oil is generally a term of art used by ingredient suppliers and encompasses a range of products of varying UFA content and purity.

The term "nitric oxide releasing compounds" or "NORC" means any compound or compounds that cause or can result in the release of nitric oxide in an animal. Examples of such compounds include L-arginine, L-arginine-containing peptides and proteins, and analogs or derivatives thereof that are known or determined to release nitric oxide, such as arginine alpha-ketoglutarate, GEA 3175, sodium nitroprusside, glyceryl trinitrate, S-nitroso-N-acetyl-penicillamine, nitroglycerin, S-NO-glutathione, NO-conjugated non-steroidal anti-inflammatory drugs (e.g., NO-naproxen, NO-aspirin, NO-ibuprofen, NO-Diclofenac, NO-Flurbiprofen, and NO-Ketoprofen), NO-releasing compound-7, NO-releasing compound-5, NO-releasing compound-12, NO-releasing compound-18, diazenium diolates and derivatives thereof, diethylamine NONOate, and any organic or inorganic compound, biomolecule, or analog, homolog, conjugate, or derivative thereof that causes the release of nitric oxide, particularly "free" NO, in an animal. NORC are also defined to include supplements that can be converted to nitric oxide releasing compounds when metabolized in the body, e.g., citrulline and ornithine.

The term "visual system" includes any or all components) that contribute to an animal's visual sense, i.e., the perception, acquisition, or processing of any visual signal or information that may be perceived, processed, understood or acted upon based on input from an animal's vision. Preferably, for various embodiments, the visual system means one or more of the eyes, particularly the neural-derived tissues thereof (e.g., the retina), the optic nerve, and optionally, various aspects of the central nervous system involved in processing visual signals or visual inputs. It will be understood that as used herein, the visual system can be broader than, e.g., the eyes, or the eyes and the optic nerve. In particular, it is contemplated herein that the methods and compositions of the invention may be useful to treat, reduce or decrease, or prevent deterioration in one or more of the eyes, particularly the retina, the optic nerve, the optic chiasm, the optic tract(s), the lateral geniculate nucleus (LGN) and/or related tissues of the thalamus, the superior colliculus, the optic radiations, the primary visual cortex of the brain (V1), and/or higher cortex regions involved in processing visual information. Other areas of the central nervous system that are contemplated as part of the vision system for purposes herein include the prestriate cortex (V2), third visual complex (including V3), visual area V4, visual area V5 (aka "visual area MT"), pretectal nucleus, and superchiasmatic nucleus.

The term "age-related deterioration of vision" means a natural decline or loss of one or more aspects of an animal's visual perception, acquisition, or processing that may occur with normal (i.e., non-pathologic) aging in that animal or species of animal, i.e., not as a result or consequence of active disease or physical injury to the visual system of the animal. "Deterioration of vision" or "deterioration of a component of a visual system" includes deterioration of one or more anatomical, physiological, neurological, biochemical, or other properties of any part of the eye, particularly the retina, the optic nerve, or aspect of the brain (e.g., the visual cortex, and/or other aspect of the central nervous system involved in vision) associated with vision, particularly including the retina, optic nerve, optic chiasm, the optic tract, the lateral geniculate nucleus (LGN) and/or related tissues of the thalamus, the superior colliculus, the optic radiation, the primary visual cortex of the brain (V1), the prestriate cortex (V2), the third visual complex (including V3), visual area V4, visual area V5, the pretectal nucleus, or the superchiasmatic nucleus. Aspects of vision that may decline or deteriorate with age include any aspects of either perception, acquisition, or processing of visual information, i.e., any aspect of visual acuity, or visual discrimination, and the processing of such information, including changes in: the shape of the eyeball and/or refractive errors (e.g., presbyopia, myopia, hyperopia, astigmatism, etc., leading to near-sightedness, far-sightedness and the like); the presence of cataracts, floaters, and the like; pupil size; photoreceptors (loss or alteration thereof); depth perception; color perception; motion perception; contrast sensitivity and/or ability to distinguish light and dark; ability to locate, identify, or avoid objects (including visual search functions, and spatial relationships); ability to distinguish figure from ground; ability to process visual information or perform tasks associated with visual input; problem solving related to visual information; ability to recall visual information; ability to track an object; response times of the visual system or parts thereof, such as time to focus, pupillary response time to a stimulus, time to adjust to any new visual input (e.g., change in light or other input), time to process a visual input, blink rate, blink interval, and blink response time to a stimulus; and the like. In addition, age-related alteration or deterioration (physical or otherwise) of particular cells, cell types, or tissues can result in decline or loss of one or more aspects of vision, for example, even a minor change in structure in the retina with age can potentially result in profound effects on the animal's vision. Deterioration of a component of the visual system can be measured relative to a control, a cohort, or relative to an earlier time-point for the same individual in the case of certain types of deterioration, e.g., age-related visual decline.

The term "disease-related deterioration of vision" means a decline or loss of any aspect(s) of an animal's visual perception, acquisition, or processing that may occur as a result of a disease condition in that animal or species of animal. Disease-related deterioration of vision includes deterioration or loss of any anatomical, physiological, neurological biochemical, or other properties of any part of the eye or brain associated with vision, including the retina and optic nerve. Many diseases are known to affect the visual system of animals. Some examples of diseases known to cause such deterioration include glaucoma, macular degeneration, Alzheimer's Disease, various retinopathies, such as diabetic retinopathy, and schizophrenia.

The term "retina" is a common short-hand term for a highly-organized and complex multilayer structure of the visual system. The retina comprises at least five different kinds of neurons including photoreceptors, bipolar cells, horizontal cells, amacrine cells, and ganglions. There are one or more, and in some cases many types of each of the foregoing. Communication within the retina occurs in at least two directions: (a) across layers (e.g., as light energy is received and converted to useful electrical signals which are sent to the brain for processing), and (b) laterally throughout a particular layer or layers. It is useful and instructive to understand the anatomical structures encompassed within the term "retina" which skilled artisans will readily appreciate. Thus, as used herein, "retina" includes the inner retinal layer, which is proximal to the vitreous of the eye, as well as the outer retinal layer, proximal to the choroid (i.e., the vascular/connective layer between the retina and the sclera of the eye), and the layers therebetween. Each of these layers comprises one or more cell portions or types that are involved directly or indirectly in processing of visual information. Beginning at the outermost layer and moving inward toward the vitreous, the retina comprises at least the following layers: The outermost layer of the retina is the retinal pigment epithelium ("RPE") which provides vital metabolic support to other retinal layers but is not directly involved in encoding visual stimuli into neurological signals, and is not responsive to light. RPE cells are darkly pigmented and absorb stray photons that would otherwise contribute to light scatter within the eye. The next few layers of the retina relate to various cell bodies or portions, including those of the photoreceptor cells, i.e., rods for night vision and cones for day vision. Photoreceptors are the cells that receive light and transduce visual information signals for processing. Photoreceptors have a metabolic rate that is among the highest of any cells in the body. The metabolic needs of these cells are accommodated by having these cells located near the choroidal blood supply. The outer aspect of photoreceptors is a distinct layer called the outer segment. This layer contains photopigments which absorb light and convert it into electrical signals. The next layer of the retina is the inner segment of the photoreceptors, which contains many of the non-nuclear organelles of the photoreceptors. The outer limiting membrane ("OLM"), formed by interconnecting processes of retinal glial cells (aka Müller cells), separates the inner segment of the photoreceptor cells from their nuclei. The photoreceptor nuclei form the next distinct retinal layer, referred to as the outer nuclear layer ("ONL"). Continuing inward, the next retinal layer is the outer plexiform layer ("OPL") which comprises the first layer of synaptic structures encountered, including dendrites of bipolar and horizontal layers, the synaptic endings of the photoreceptors, and other synapses. The inner nuclear layer ("INL") is the next retinal layer, comprising bodies of the bipolar and horizontal cells, as well as the bodies of various types of amacrine cells. The next layer is the inner plexiform layer ("IPL") comprising synapses of bipolar, horizontal, and amacrine cells. The innermost cell body layer is the ganglion cell layer ("GCL") which is comprised of from about 80% parvo (or midget) cells, from about 10% parasol or macro cells, and other ganglion cells. The next layer of the retina, the nerve fiber layer ("NFL") comprises the axons of the ganglion cells. These nerves are not myelinated within the eye, however they become so as they leave the eye to form the optic nerve. The innermost layer of the retina is the internal limiting membrane ("ILM"), which separates the retina from the vitreous humor.

The term "optic nerve" means the second cranial nerve, or any portion thereof. The optic nerve is formed by the retinal ganglion cell axons of ganglion cells as they exit the eye, as well as certain support cells. The optic nerve is not actually a nerve, but rather an integral part of the central nervous system, featuring a myelin covering produced by oligodendrocytes, and being encased within all three meningeal layers (dura mater, arachnoid mater, and pia mater layers). The optic nerve head (or optic disk) can be observed clinically and is a prominent feature of the fundus, which is the name of the structure comprising the retina and other ocular structures as viewed via opthalmoscopy. The optic nerve head is characterized by its whitish appearance as a result of the myelin sheath covering the nerves as they exit the eye.

As used herein, the term "treating, reducing, or preventing" refers to degrees or types of beneficial or therapeutic effect from the compositions and/or methods disclosed herein. In particular, "treating" deterioration generally indicates that some amount of deterioration, damage, loss, or decline has already occurred, and a method or composition is useful for ameliorating to some extent, one or more symptoms or results of the associated deterioration, damage, loss, or decline, i.e., after the fact. "Treating" also indicates that the given composition or method may not be effective at minimizing or short-circuiting any potential deterioration, damage or decline. Reducing deterioration generally indicates that the composition or method in question is capable of some degree lessening the deterioration, damage, or decline before it happens; i.e., it has at least a partial preventative effect. A reducing effect may be observed in terms of the type and/or the extent of deterioration, damage, loss, or decline. "Preventing" deterioration indicates that the composition or method in question is capable of preventing one or more results of deterioration, damage, loss, or decline in a visual system, i.e., the composition or method is at least partially preventative and may be completely so. "Preventing" may be related to the type or extent of damage, or may also be associated with a delay in onset of deterioration (i.e., the prevention need not be "permanent" for the animal to benefit, as the prime years may be extended, and/or the quality of life may be enhanced). Thus, at a minimum an "effective" composition or method is capable of treating deterioration to provide some positive effect after the fact of deterioration. Preferably, the composition or method has a reducing effect and is capable of at least some preventative effect. More preferably, a composition or method is at least partially capable of fully preventing one or more aspects of deterioration, damage, or decline that would otherwise likely occur to an animal's visual system.

As used herein, the term "food" or "food composition" means a composition that is intended for ingestion by an animal, including a human, and provides nutrition thereto. As used herein, a "food product formulated for human consumption" is any composition specifically intended for ingestion by a human being. "Pet foods" are compositions intended for consumption by pets, particularly by companion animals. A "complete and nutritionally balanced pet food" is one that contains all known required nutrients for the intended recipient or consumer of the food, in appropriate amounts and proportions, based for example on recommendations of recognized authorities in the field of companion animal nutrition. Such foods are therefore capable of serving as a sole source of dietary intake to maintain life or promote production, without the addition of supplemental nutritional sources.

Nutritionally balanced pet food compositions may be a "wet food", "dry food", or food of intermediate moisture content. "Wet food" describes pet food that is typically packaged in cans or foil bags, and has a moisture content generally in the range of from about 70 to about 90%. "Dry food" describes pet food that may be similar in nutrient composition to wet food, but contains a limited moisture content. Dry food is typically in the range of from about 5 to about 20%, and therefore may be presented, for example, as small biscuit-like kibbles. In one presently preferred embodiment, the compositions have moisture content from about 5 to about 20%. Dry food products include foods of moisture content in or about the stated range, such that they are substantially resistant to microbial or fungal deterioration or contamination under normal conditions of storage.

As used herein, a "dietary supplement" is a food that is intended to be ingested in addition to the normal diet of an animal. Dietary supplements may be in any form—e.g., solid, liquid, gel, tablets, capsules, powder, and the like. Preferably, they are provided in convenient dosage forms. In some embodiments, they are provided in bulk consumer packages such as bulk powders or liquids. In other embodiments, supplements are provided in bulk quantities to be included in other food items such as snacks, treats, supplement bars, beverages and the like.

The term "effective amount" means an amount of a compound, material, composition, dietary supplement, medicament, or other material that is effective to achieve a particular biological result, such as reducing, preventing or treating deterioration of an animal's vision.

The term "Young" refers generally to an individual in young adulthood, i.e., matured past puberty or adolescence, as would be defined by species, or by strain, breed or ethnic group within a species, in accordance with known parameters. "Aged" or "old," as used herein, refers to an individual who is physically or chronologically within about the last 30% of its average life expectancy, as determined by species, or by strain, breed, or ethnic group within a species, in accordance with known parameters. Skilled artisans will appreciate that in general usage "aging" is a process that all living organisms are undergoing, and simply refers to the fact that any living animal is growing older than that animal was previously. As will be clear from the context, the term "aging" as used herein is generally substantially synonymous with "aged" as defined above and thus indicates an animal that is within about the last 30% of its average life expectancy for its kind.

As used herein, the "prime years" of an animal's life can extend from young adulthood ("young," as described above) into the older or "aged" population. Indeed, the prime years of an animal's life can extend essentially until the animal's death, assuming the animal is healthy and active through its older years.

The term "extending the prime" means extending the number of years an animal lives a healthy life and not just extending the number of years an animal lives, e.g., an animal receiving a treatment that extends the prime would be healthy in the prime of its life for a longer time, relative to another animal not receiving the treatment.

The term "health and/or wellness of an animal" means the complete physical, mental, and social well being of the animal, not merely the absence of disease or infirmity.

The term "regular administration" as used herein with respect to the compositions disclosed herein means providing a regular dose of the composition to an animal. Skilled artisans will appreciate that dosing frequency will be a function of the substance that is being administered, and some compositions may require or allow for more or less frequent administration to maintain a desired biochemical, physiological, or gene expression effect, or the like, including neurological and neuroanatomical effects. One goal of regular administration is to provide the animal with a regular and/or consistent dose of the composition or the direct or indirect metabolites that result from such ingestion. Regular and/or consistent dosing will preferably increase blood levels of the components of the compositions or their direct or indirect metabolites compared to those of an animal not receiving administration of the compositions, or even more preferably result in a constant blood level of the those components and/or metabolites. "Regular basis" thus refers to at least monthly administration. "Regular administration" can be once monthly, once weekly, or once daily. Administration can be more frequent than once daily, such as multiple times per day. Administration on other bases is also contemplated, such as every other day, every other week, or every other month, every third day, week, or month, every fourth day, week, or month, and the like. Any dosing frequency, regardless of whether expressly exemplified herein, may be deemed useful for particular applications. The term "extended regular basis" as used herein refers to long-term administration of a substance on a regular basis.

"Long term" administration as used herein generally refers to periods in excess of one month. Periods of longer than two, three, or four months are contemplated. Also included are more extended periods that include longer than 5, 6, 7, 8, 9, or 10 months. Periods in excess of 11 months or 1 year are also included. Longer terms use extending over 1, 2, 3, or more years are also contemplated herein. In the case of certain animals, it is envisioned that the animal would be administered substances identified by the present methods on a regular basis or extended regular basis.

The term "in conjunction with" means that a drug, supplement, food, or other substance is administered to an animal (1) together, e.g., in a composition, particularly a food composition, or (2) separately, e.g., at the same or different time, and/or the same or different frequency, using the same or different administration routes. When administration is "separate" the drug, supplement, food, or other substance can be also given about the same time or periodically. "About the same time" generally means that the substance (e.g., food or drug) is administered at the same time or within about 72 hours of each other. "Periodically" means that the substance is administered on a dosage schedule acceptable for a specific substance. "In conjunction" specifically includes administration schemes wherein substances such as drugs are administered for a prescribed period and compositions of the invention are administered indefinitely. Administration of a composition consistent herewith can be direct or indirect, e.g., in connection with a dietary regimen for the animal. When utilized as a supplement to ordinary dietary requirements, a composition may be administered directly to the animal. The compositions can alternatively be contacted with, or admixed with, daily feed or food, including a fluid such as drinking water, or an intravenous connection for an animal that is receiving such treatment.

As used herein, the term "oral administration" or "orally administering" means that an animal ingests, or a human is directed to feed, or does feed, the animal one or more of the substances described herein. The term "ingestion" is used herein interchangeably with the term "oral administration." Wherein a human is directed to orally administer or feed the substance, such direction may be that which instructs and/or informs the human that use of the substance may and/or will provide the referenced benefit. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, or other computer-related media), and/or packaging associated with the substance.

The term "topical administration" as used herein, means the administration or application of a composition to the skin, mucosa, eye, or any other epithelial surface.

The term "sample" means any animal tissue or fluid containing, e.g., polynucleotides, polypeptides, antibodies, metabolites, and the like, including cells and other tissue containing DNA and RNA. Examples include adipose, blood, cartilage, connective, epithelial, lymphoid, muscle, nervous, sputum, and the like. A sample may be solid or liquid and may be or contain DNA, RNA, cDNA, tissue(s), bodily fluids such as blood or urine, cells, cell preparations or fractions thereof, chromosomes, organelles, and the like.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

All percentages expressed herein are by weight of the composition on a dry matter (or "dry weight") basis unless specifically stated otherwise. Skilled artisans will appreciate that the terms "dry matter basis" or "dry weight basis" mean that the amount of the ingredient present in the composition is expressed relative to the composition after the free moisture in the composition is removed.

Dosages expressed herein are generally indicated as milligrams or grams per kilogram of body weight (mg/kg or g/kg) unless expressed otherwise.

As used herein, ranges are used herein in shorthand, to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a compound" or "a method" includes a plurality of such "compounds" or "methods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context.

The terms "comprising" or "including" are intended to include embodiments encompassed by the terms "consisting essentially of" and "consisting of". Similarly, the term "consisting essentially of" is intended to include embodiments encompassed by the term "consisting of".

The methods and compositions and other advances disclosed here are not limited to particular methodology, protocols, and reagents described herein because, as skilled artisans will appreciate, they may vary. Further, the terminology used herein is for describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for treating, reducing, or preventing deterioration of one or more components of the visual system of an animal. The methods comprise identifying an animal susceptible to or suffering from deterioration of one or more components of the visual system and administering in conjunction to the animal one or more unsaturated fatty acids (UFA) and one or more nitric oxide releasing compounds (NORC) in an amount effective for treating, reducing, or preventing deterioration of such visual system components.

The invention is based in part upon the discovery that a combination of UFA and NORC are useful for treating, decreasing, or preventing deterioration in an animal's vision system, particularly deterioration that results from normal aging, disease, or injury. In particular, and as described in greater detail below and in the examples, methods have been developed based on administering such compounds to animals whereby the deterioration of one or more aspects of vision is altered, prevented, or reversed.

In various embodiments, the deterioration of the visual system includes deterioration of one or more of the retina, the optic nerve, or another component of the visual system. In certain preferred embodiments, the deterioration is of the retina or optic nerve. In particular embodiments, the deterioration comprises deterioration in any of the physiological or functional layers of the retina. Such layers can be seen by visual observation for example using microscopy methods and the like. Deterioration of interest can occur in one or more such layers including but not limited to the retinal pigment epithelium, the outer segment (photoreceptors), the inner segment (photoreceptors), the outer limiting membrane, the outer nuclear layer, the outer plexiform layer, the inner nuclear layer, the inner plexiform layer, the ganglion cell layer, the nerve fiber layer, or the inner limiting membrane.

In other embodiments, other components of the visual system may be subject to deterioration, such as one or more of the optic chiasm, the optic tract, the lateral geniculate nucleus (LGN) and/or related tissues of the thalamus, the superior colliculus, the optic radiation, the primary visual cortex of the brain (V1), the prestriate cortex (V2), the third visual complex (including V3), visual area V4, visual area V5, the pretectal nucleus, or the superchiasmatic nucleus.

The visual system deterioration may be caused by normal aging, such that there appears to be an absence of an injury or disease that is identifiable as a substantial source of the deterioration. Skilled artisans will understand the established methods for diagnosing such disease states, and/or inspecting for known signs of such injuries. In addition, the literature is replete with information on age-related decline or deterioration in aspects of the visual systems of animals.

Additionally or alternatively, the deterioration of the visual system components, such as the retina and/or optic nerve can be caused by injury, for example trauma to the visual system itself (e.g., an eye), to the head or brain, or the body more generally. Certain such injuries are known to be age-related injuries, i.e., their likelihood, or frequency increases with age.

Examples of such injuries include retinal tears, macular holes, epiretinal membrane, and retinal detachments, each of which might occur in an animal of any age, but which are more likely to occur, or occur with greater frequency in aging animals, including otherwise healthy aging animals.

The deterioration of the visual system or components thereof also can be caused by disease. Included among the diseases are various age-related diseases that impact the visual system. Such diseases occur with greater likelihood and/or frequency in older animals than in the young. Examples of diseases which may affect the visual system, including for example the retinal layers and optic nerve, and cause deterioration thereof are various forms of retinitis, optic neuritis, macular degeneration, proliferative or nonproliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage (preretinal, intraretinal and/or subretinal), hypertensive retinopathy, retinal inflammation, retinal edema, retinoblastoma, or retinitis pigmentosa.

Some of the foregoing diseases tend to be specific to certain animals such as companion animals, e.g., dogs and/or cats. Some of the diseases are listed generically, i.e., there may be many types of retinitis, or retinal hemorrhage; thus some of the disease are not caused by one specific etiologic agent, but are more descriptive of the type of disease or the result. Many of the diseases that can cause decline or deterioration of one or more components of the visual system can have both primary and secondary or more remote effects on an animal's visual system.

In various embodiments, the methods are directed to humans or companion animals, such as dogs and cats. The animal can be an aged animal, and the methods are particularly well suited to aged (aging) animals because of the propensity of aging animals to suffer deterioration or decline in at least one component of their visual system, for example, the retina and/or optic nerve.

The UFA useful in the invention are any type or from any source. In particular embodiments, the UFA are one or more of ALA, EPA, DPA, DHA, or another n-3 fatty acid from any source, e.g., natural or synthetic. Fish oils are well-known and popular sources of UFA, particularly long-chain polyunsaturated fatty acids (LCPUFA) for use in foods and supplements.

The UFA are administered to the animal in amounts of from about 0.001 to about 50 g/kg, although greater or lesser amounts can be administered. In various embodiments, the UFA are administered in amounts of from about 0.001 to about 25 g/kg, from about 0.001 to about 10 g/kg, or from about 0.001 to about 5 g/kg. Preferably, the UFA are administered in amounts of from about 0.001 to about 1 g/kg, more preferably from about 0.001 to about 0.5 g/kg. When administered in a composition, the composition comprises from about 0.1 to about 50% UFA. More preferably, the UFA content is from about 0.5 to about 20%, from about 1 to about 10%, or from about 2 to about 5%. In some embodiments, the acceptability of the composition from a sensory perspective may decrease as the content of the UFA goes up, and thus at high concentrations, sensory attributes such as flavor or aftertaste may be considered in formulating the compositions.

The NORC useful in the invention are any type from any source. In particular embodiments, the NORC are arginine or a nitric oxide-releasing analog or derivative of arginine. In other embodiments, citrulline or ornithine are used as a source of NORC.

The NORC are administered to the animal in amounts of from about 0.001 to about 50 g/kg, although greater or lesser amounts can be administered. In various embodiments, the NORC are administered in amounts of from about 0.001 to about 25 g/kg, from about 0.001 to about 10 g/kg, or from about 0.001 to about 5 g/kg. Preferably, the NORC are administered in amounts of from about 0.001 to about 1 g/kg, more preferably from about 0.001 to about 0.5 g/kg. When administered in a composition, the composition preferably comprises from about 0.1 to about 20% NORC. Other compositions may comprise, for example, from about 0.5 to about 15%, from about 1 to about 10%, or from about 2 to about 5% NORC.

In various embodiments, the methods for using UFA and NORC for treating, reducing, or preventing deterioration of one or more components of the visual system further comprise administering in conjunction to the animal one or more B vitamins, one or more antioxidants, or a combination of B vitamins and antioxidants in an amount effective for treating, reducing, or preventing the deterioration. In preferred embodiments, the methods further comprise administering in conjunction to the animal one or more B vitamins and one or more antioxidants in an amount effective for treating, reducing, or preventing the deterioration. Generally, the B vitamins are administered in an amount of from about 0.1 to about 40 times the recommended daily requirement of B vitamins, preferably from about 0.5 to about 20 times the recommended daily requirement of B vitamins, and the antioxidants are administered in an amount of from about 0.1 to about 10 times the recommended daily allowance for the antioxidants, preferably from about 0.5 to about 5 times the recommended daily allowance. When administered in a composition, the composition preferably comprises from about 0.1 to about 40 times the recommended daily requirement of B vitamins and from about 0.1 to about 10 times the recommended daily allowance for the antioxidants.

In various embodiments, the methods are useful to treat deterioration of the visual system of an animal, e.g., to help mitigate one or more aspects of damage after it has occurred. In preferred embodiments, the methods are useful to reduce the deterioration than would otherwise occur in the absence of such methods. More preferably, the methods are useful for preventing some, substantially all or all deterioration to the visual system of an animal. Other preferred embodiments feature methods that delay the onset of one or more aspects of deterioration, wherein the longer the delay to onset, the more preferred the embodiment. Still other embodiments feature methods that can partially or fully reverse one or more aspects of the deterioration of the visual system. Skilled artisans will appreciate that the longer damage has gone untreated, the more difficult is the treating, decreasing, or prevention of that or other damage to the visual system. Preferably the methods are applied to at risk animals, e.g., aging animals prior to the deterioration of the visual system, or at a time when damage or decline is minimal.

The compositions for use herein optionally comprise one or more supplementary substances that contribute to the observed effect of treating, reducing, or preventing deterioration of a component of the visual system, or which promote or sustain general health and wellness, as would be appreciated by skilled artisans. The compositions may thus further comprise substances such as minerals, other vitamins, salts, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium and the like. Examples of additional vitamins useful herein include such fat-soluble vitamins as A, E, and K. Inulin, amino acids, enzymes, coenzymes, and the like may be useful to include in various embodiments.

In certain embodiments, compositions comprise UFA and NORC. In others, compositions consist essentially of UFA and NORC. In yet others, compositions consist of UFA and NORC. In various embodiments, the compositions comprise, consist essentially of, or consist of UFA and NORC and either B vitamins, antioxidants, or a combination thereof.

Any antioxidant suitable for administration to an animal is contemplated for use herein. Antioxidants are well known in the art of food technology and food formulation. Natural antioxidant compounds include the antioxidant vitamins (such as A, C and E, and derivative, conjugates, or analogs thereof). Compounds such as α-lipoic acid, chlorophyll and derivatives thereof, glutathione, ubiquinols (e.g., coenzyme Q10), carotenoids (e.g., lycopene), flavonoids, phenolics, and polyphenols, and pycnogenol are known to be excellent antioxidants, and most can be derived from one or more plant sources. Many plant extracts, including extracts from flowers, fruit, vegetables, herbs, seeds, bark, stems, shoots, roots and/or other parts of plants are known to contain useful antioxidants. Specific examples of plant sources of antioxidants include fruits such as berries (e.g., elderberry, cherry, blackberry, strawberry, raspberry, cranberry, crowberry, blueberry, bilberry/wild blueberry, black currant), pomegranate, grape, orange, plum, pineapple, kiwi fruit, citrus (including, for example, lemon and grapefruit), dried fruits like apricots, prunes, and dates; and vegetables, such as cruciferous vegetables (for example kale, cabbage, Brussels sprouts, broccoli, and bok choy), parsley, artichoke, spinach, ginger, garlic, beets, peppers (including chili and other 'hot' peppers). Also good sources of plant antioxidants are nuts and seeds such as pecans, walnuts, hazelnuts, ground nuts, and sunflower seeds, grape seeds; legumes, including soy, broad, and pinto beans for example; cereals such as barley, millet, oats, and corn. Natural antioxidants are also derived from a wide variety of spices including cloves, cinnamon, rosemary, and oregano. Less widely known sources of antioxidants include Ginkgo biloba, and tropical plants such as uyaku, and *carica papaya*. Certain other antioxidants have become of great interest in recent years and would be suitable for use herein, including those from various fermented and unfermented teas and green tea, fermented products such as red wine, and so-called "superfruits" such as noni, mangosteen, acai, mango, goji, sea-buckthorn, and others. Selenium is an excellent oxygen scavenger and works well, especially with vitamin E compounds and/or related tocopherol and/or tocotrienol compounds. Synthetic dietary antioxidants include butylated hydroxyanisole (BHA) and butylated hydroxytoluene (BHT) which are commonly used in food products. Any of the foregoing, alone or in combination, are suited for use herein, as are combinations of natural and synthetic antioxidants. In one embodiment, the antioxidants comprise astaxanthin alone or in combination with other antioxidants.

Preferred antioxidants include one or more of the antioxidant vitamins (e.g., A, C, and E), or a tocopherol or tocotrienol compound that has similar or better antioxidant properties and preferably also has vitamin E activity. Other preferred antioxidants include zeaxanthin, astaxanthin, lutein, or selenium. Selenium is particularly useful when vitamin E compounds (including tocopherols and tocotrienols) are present in the formulation.

In various embodiments, the UFA, NORC, B vitamins, and/or antioxidants are administered to the animal on a long-term basis, preferably on an extended regular basis. Preferably, the UFA, NORC, B vitamins, and/or antioxidants are administered to the animal on a regular basis, preferably daily.

The methods provided are generally based on using compositions that may readily be formulated as a human food composition, a pet food composition, or a dietary supplement. Such compositions include foods intended to supply the necessary dietary requirements for a human, or a companion animal, or as animal treats (e.g., biscuits), or dietary supplements. The formulation of such compositions is readily understood by skilled artisans who will appreciate that the food compositions may further comprise protein, fat, moisture, for example, from about 15 to about 50% protein, from about 5 to about 40% fat, and a moisture content of from about 5 to about 20%. Such compositions may have from about 5 to about 10% ash content. Also, as described in greater detail below, the composition can contain additional ingredients, including vitamins, minerals, prebiotics, probiotics, or a combination thereof.

Certain aspects of the invention are preferably used in combination with a complete and balanced food. According to certain embodiments, the compositions comprising the UFA and NORC, and B vitamins and antioxidants if needed, are preferably used with or formulated into a complete and balanced commercial food. The compositions and dietary supplements may also be specially formulated for the intended recipients or consumers, such as for adult animals or for older or young animals. For example, a composition adapted for aging animals can be prepared, as can compositions adapted for the nutritional needs of active, pregnant, or lactating animals, or even, for example, for puppies or kittens. In general, specialized compositions will comprise energy and nutritional requirements appropriate for animals at different stages of development or age, or of different health or nutritional status.

In one embodiment, the composition is formulated as a refrigerated or frozen composition. In other embodiments, the composition may be a dry composition (e.g., kibble), semi-moist composition, wet composition, or any mixture thereof. In another embodiment, the composition is a dietary supplement formulated as a gravy, drink, beverage, yogurt, powder, granule, paste, suspension, chew, morsel, treat, snack, pellet, pill, capsule, tablet, or any other suitable delivery form. The dietary supplement can comprise a high concentration of the UFA and NORC such that the supplement can be administered to the animal in small amounts, or in the alternative, can be diluted prior to administration to an animal. The dietary supplement may require admixing, or preferably be admixed with water or other diluent prior to administration to the animal.

In various embodiments, pet food or pet treat compositions that contain UFA and NORC, and B vitamins and antioxidants if needed, comprise from about 15 to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof. The compositions may further comprise from about 5 to about 40% fat. The compositions may further comprise a source of carbohydrate. The compositions may comprise from about 15 to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products. In some embodiments, the ash content of the composition ranges from less than 1 to about 15%, preferably from about 5 to about 10%. The moisture content can vary depending on the desired nature of the composition. In a preferred embodiment, the composition is a complete and nutritionally balanced pet food. In this embodiment, the pet food may be a "wet food", "dry food", or food of intermediate moisture content. Presently preferred are dry food compositions that are extruded food products, such as pet foods, or snack foods for either humans or companion animals. The compositions may also comprise one or more fiber sources. The term "fiber" includes all sources of "bulk" in the food whether digestible or indigestible, soluble or insoluble, fermentable or nonfermentable. Preferred fibers are from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, fructooligosaccharide, pectin, short chain oligofructose, mannanoligofructose, soy fiber, arabinogalactan, galactooligosaccharide, arabinoxylan, or mixtures thereof. Alternatively, the fiber source can be a fermentable fiber. Fermentable fiber has previously been described to provide a benefit to the immune system of a companion animal. Fermentable fiber and other compositions can act as prebiotics (as discussed below) to enhance the growth of probiotic organisms in the gastrointestinal tract.

In various embodiments, the methods further comprise administering in conjunction with the UFA and NORC (and optional B vitamins, antioxidants, or combinations thereof) at least one of (1) one or more probiotics; (2) one or more inactivated probiotics; (3) one or more components of inactivated probiotics that promote health benefits similar to or the same as the probiotics; (4) one or more prebiotics; and (5) combinations thereof. When administered with compositions, the probiotics or their components can be integrated into the compositions (e.g., uniformly or non-uniformly distributed in the compositions) or applied to the compositions (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli, Bifidobacteria*, or *Enterococci*, e.g., *Lactobacillus reuteii, Lactobacillus acidophilus, Lactobacillus animalis, Lactobacillus ruminis, Lactobacillus johnsonii, Lactobacillus casei, Lactobacillus paracasei, Lactobacillus rhamnosus, Lactobacillus fermentum,* and *Bifidobacterium* sp., *Enterococcus faecium* and *Enterococcus* sp. In some embodiments, the probiotic strain is selected from the group consisting of *Lactobacillus reuteri* (NCC2581; CNCM I-2448), *Lactobacillus reuteri* (NCC2592; CNCM I-2450), *Lactobacillus rhamnosus* (NCC2583; CNCM I-2449), *Lactobacillus reuteri* (NCC2603; CNCM I-2451), *Lactobacillus reuteri* (NCC2613; CNCM I-2452), *Lactobacillus acidophilus* (NCC2628; CNCM I-2453), *Bifidobacterium adolescentis* (e.g., NCC2627), *Bifidobacterium* sp. NCC2657 or *Enterococcus faecium* SF68 (NCIMB 10415). The probiotics are administered in amounts sufficient to supply from about $10^4$ to about $10^{12}$ cfu/animal/day, preferably from $10^5$ to about $10^{11}$ cfu/animal/day, most preferably from $10^7$ to $10^{10}$ cfu/animal/day. When the probiotics are killed or inactivated, the amount of killed or inactivated probiotics or their components should produce a similar beneficial effect as the live microorganisms. Many such probiotics and their benefits are known to skilled artisans, e.g., EP1213970B1, EP1143806B1, U.S. Pat. No. 7,189,390, EP1482811B1, EP1296565B1, and U.S. Pat. No. 6,929,793. In a preferred embodiment, the probiotic is *Enterococcus faecium* SF68 (NCIMB 10415). In one embodiment, the probiotics are encapsulated in a carrier using methods and materials known to skilled artisans.

As stated, the methods may use one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isomaltulose. Fructo-oligosaccharides are found naturally in many foods such as wheat, onions, bananas, honey, garlic, and leeks. In one embodiment, the prebiotic is chicory root, chicory root extract, inulin, or combinations thereof. Generally, prebiotics are administered in amounts sufficient to positively stimulate the healthy microflora in the gut and cause these "good" bacteria to reproduce. Typical amounts are from about one to about 10 grams per serving or from about 5 to about 40% of the recommended daily dietary fiber for an animal. The amount of prebiotic can be determined by skilled artisans based upon (1) the type and nature of the prebiotic and the type and nature of the desired composition and (2) the type and nature of the animal that will consume the prebiotics, e.g., the animal's age, weight, general health, sex, gut microflora status (including presence of harmful bacteria), and diet.

The probiotics and prebiotics can be made part of a composition by any suitable means. Generally, the agents are mixed with the composition or applied to the surface of the composition, e.g., by sprinkling or spraying. When the agents are part of a kit, the agents can be admixed with other materials or in their own package. Typically, the food composition contains from about 0.1 to about 10% prebiotic, preferably from about 0.3 to about 7%, most preferably from about 0.5 to 5%, on a dry matter basis. The prebiotics can be integrated into the compositions using methods known to skilled artisans, e.g., U.S. Pat. No. 5,952,033.

The probiotics may be administered in any effective amount for any duration, whether short or preferably longer term, and at any useful frequency. In one embodiment, the methods employ compositions that are administered on an extended regular basis, preferably on a daily basis. According to the methods of the invention, administration of the compositions, including administration as part of a dietary regimen, can span a period ranging from parturition through the adult life of the animal.

In certain embodiments, the animal is a young or growing animal. In other embodiments, the animal is an adult or mature animal. In other embodiments, the animal is an aging animal. An animal that has reached about 30% of its projected lifespan is generally suitable. In certain embodiments, administration begins, for example, on a regular or extended regular basis, when the animal has reached more than about 30, 40, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

The methods described herein may also employ pharmaceutical or nutraceutical compositions, formulated for administration by any selected route, as described in greater detail below.

In some embodiments, the compounds or compositions of the invention are administered to the animal in conjunction with one or more therapeutic agents useful for, and in an amount effective for, treating, reducing, or preventing deterioration of one or more components of the visual system of an animal. Therapeutic agents useful for treating, reducing, or preventing deterioration of a visual system component, one or more of these agents may be useful: an Age-Related Eye Diseases Study (AREDS) vitamin formulation, a macular carotenoid, a VEGF or VEGF receptor inhibitory compound, an intravitreal steroid, a steroid analogue, a tyrosine kinase inhibitor, an anti-angiogenesis compound, or a protein kinase C inhibitor. VEGF inhibitory compounds are preferably an aptamer, an antibody, an RNAi compound, a receptor blocker, or a tyrosine kinase inhibitor. Specific agents contemplated for use herein include: pegaptanib (MACUGEN, Eyetech/Pfizer), verteporfin (VISUDYNE, Novartis/QLT), bevacizumab (AVASTIN, Genentech), ranibizumab (LUCENTIS, Genentech), VEGF Trap (Regeneron Pharmaceuticals), anecortave acetate (RETAANE, Alcon), squalamine (EVIZON, Genaera), Sirna-027(Sirna Therapeutics), Cand5 (Acuity Pharmaceuticals), ganciclovir, ruboxistaurin mesylate (Eli Lilly and Co.), or hyaluronidase (e.g., VITRASE, Ista Pharmaceuticals), some of which are on the market and some of which are still in clinical trials.

The composition administered in the methods is a pharmaceutical or nutraceutical composition in certain embodiments, and optionally comprises one or more of the foregoing agents useful for treating, reducing, or preventing the deterioration of a visual system component.

In another embodiment, the invention provides pharmaceutical compositions comprising the compounds or compositions of the invention as described above, and one or more pharmaceutically acceptable carriers, diluents, or excipients. Generally, pharmaceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing pharmaceuticals and formulating compositions that are suitable for administration to an animal as pharmaceuticals.

The pharmaceutical composition can be formulated for any mode of administration. In one embodiment, the pharmaceutical composition is formulated for oral administration. In another embodiment, the composition is formulated for topical administration. Suitable topical formulations may include solutions, emulsions, creams, ointments, gels, liposomes, biodegradable microparticles, and other such delivery vehicles as would be well understood by the pharmaceutical chemist.

In other embodiments, the compounds or compositions are administered to the animal in conjunction with one or more physical treatments useful for treating, reducing, or preventing the deterioration of a visual system component. Again, preferably in such methods the deterioration of the visual system comprises deterioration of one or more of the retina, the optic nerve, or another component of the visual system. The physical treatment can be any treatment known for such purpose, for example, rheotherapy, or photodynamic therapy. Rheotherapy, still the subject of much debate, is similar to dialysis in theory except that the patient's blood plasma is filtered to remove toxic proteins and other substances, theoretically allowing increased blood flow to the macula. Photodynamic Therapy has not proven useful as a monotherapy for certain visual system issues, but current research indicates it has potential when used in combination with other medicaments.

Such physical treatments can be administered further in conjunction with one or more therapeutic agents also useful for treating, reducing, or preventing the deterioration. As described above, therapeutic agents related visual system deterioration include one or more of an Age-Related Eye Diseases Study (AREDS) vitamin formulation, a macular carotenoid, a VEGF or VEGF receptor inhibitory compound, an intravitreal steroid, a steroid analogue, a tyrosine kinase inhibitor, an anti-angiogenesis compound, or a protein kinase C inhibitor. Particular drugs contemplated for use herein include pegaptanib, verteporfin, bevacizumab, ranibizumab, VEGF Trap (Regeneron Pharmaceuticals), anecortave acetate, squalamine, Sirna-027, Cand5, ganciclovir, ruboxistaurin mesylate, and/or hyaluronidase. Each of the foregoing may be used in accordance with the present methods, alone or in combination.

In another aspect, the invention provides kits suitable for treating, reducing, or preventing deterioration of at least one component of the visual system of an animal. The kits comprise in separate containers in a single package or in separate containers in a virtual package, as appropriate for the kit component, one or more UFA one or more NORC. In various embodiments, the kits further comprise one or more of (1) one or more other ingredients suitable for consumption by an animal; (2) one or more B vitamins; (3) one or more antioxidants; (4) one or more therapeutic agents useful for treating, reducing, or preventing deterioration of an animal's visual system; (5) one or more prebiotics; (6) one or more probiotics; (7) one or more diagnostic devices suitable for determining whether an animal could benefit from methods and compositions for treating, reducing, or preventing deterioration of at least one component of the visual system; (8) instructions for how to combine or prepare the UFA, NORC, and any other ingredients provided in the kit for administration to an animal; (9) instructions for how to use one or more of the kit components in combination, prepared, or otherwise for the benefit of an animal; and (10) a device for administering the combined or prepared kit components to an animal.

In one embodiment, the kits contain the UFA and NORC in a composition and contain one or more of the other kit components. In other embodiments, the kits contain the UFA and NORC and one or more of B vitamins and antioxidants in a composition and contain one or more of the other kit components. In a preferred embodiment, the kit contains the UFA, NORC, B vitamins, and antioxidants in a composition and contains one or more of the other kit components. In preferred embodiments, the composition is a food composition suitable for consumption by an animal.

The kits are particularly useful where the deterioration of the visual system comprises deterioration of one or more of the retina, the optic nerve, or another component of the visual system. Such deterioration is described more fully above, and in the definitions sections herein.

In another aspect, the invention provides means for communicating information about or instructions for one or more of (1) using the disclosed methods or compositions for treating, reducing, or preventing deterioration of at least one component of the visual system; (2) admixing the UFA, NORC, B vitamins, antioxidants, or other components disclosed herein to produce a composition suitable for treating, reducing, or preventing deterioration of a component of the visual system in the animal; (3) using the disclosed kits for treating, reducing, or preventing deterioration of a component of the visual system in the animal; or (4) administering the compositions to an animal; the means comprising one or more of a physical or electronic document, digital storage media, optical storage media, audio presentation, audiovisual display, or visual display containing the information or instructions.

The means is preferably a displayed website, a visual display kiosk, a brochure, a product label, a package insert, an advertisement, a handout, a public announcement, an audiotape, a videotape, a DVD, a CD-ROM, a computer-readable chip, a computer-readable card, a computer-readable disk, a USB device, a FireWire device, a computer memory, or any combination thereof.

In another aspect, the invention provides methods of manufacturing a food composition comprising UFA, NORC, and one or more ingredients suitable for consumption by an animal. The methods comprise admixing one or more ingredients suitable for consumption by an animal with UFA and NORC. Alternatively, UFA and NORC can be applied separately or in combination onto the food composition, e.g., as a coating or topping. The UFA and NORC can be added at any time during the manufacture and/or processing of the food composition. This includes, for example, admixing the UFA and NORC as part of the core formulation of the "body" of the food composition or applying them as a coating, i.e., primarily to the surface of the food composition after its manufacture. The compositions can be made according to any method suitable in the art.

The ingredients suitable for consumption by an animal are preferably one or more B vitamins, and/or one or more antioxidants. The inclusion of B-vitamins and antioxidants are discussed more fully with respect to other aspects of the invention, and identical considerations apply to the methods of manufacture. Other ingredients may be included in the methods, including protein, carbohydrate, fat, moisture, fiber, pre- and probiotics, and the like. Preferred ingredients include any ingredients that promote or sustain health of an animal, or ingredients, particularly functional food ingredients that support the visual system, or can aid in the repair of deterioration of the visual system. The food compositions may be of any type or kind, and intended for consumption by any animal.

Preferably, the UFA, NORC, B vitamins, or antioxidants are in the food composition in an amount effective for treating, reducing, or preventing deterioration of one or more components of the visual system of an animal when the food is administered to the animal in at least a recommended amount.

In another aspect, the invention provides packages. The packages comprise one or more of UFA, NORC, B vitamins, and antioxidants in an amount useful for treating, reducing, or preventing deterioration of one or more components of the visual system of an animal and a label affixed to the package containing a word or words, picture, design, symbol, acronym, slogan, phrase, or other device, or combination thereof, that indicates that the contents of the package contains one or more compounds suitable for treating, reducing, or preventing deterioration of one or more components of the visual system of an animal. In various embodiments, the compounds are contained in a composition, e.g., a food composition or a pharmaceutical or nutraceutical composition.

In another aspect, the invention provides medicaments and uses therefor. The medicaments comprise UFA and NORC. Thus, the invention provides for the use of UFA and NORC to prepare a medicament for treating, reducing, or preventing deterioration of at least one component of the visual system of an animal. Preferably, the animal is a human, or a companion animal.

In certain embodiments, the medicament further comprises one or more B vitamins, one or more antioxidants, or combination thereof. As with other aspects of the invention, the medicament preferably comprises a NORC that is arginine, a nitric oxide-releasing derivative or analog of arginine, citrulline, or ornithine. The use of the medicament is preferred in embodiments where deterioration of the visual system comprises deterioration of one or more of the retina, the optic nerve, or another component of the visual system. The amount of UFA, NORC, B vitamins, and antioxidants used in the medicament is the same as the amount of such compounds given herein for the methods of the invention.

The compounds and compositions of the invention, including the pharmaceutical compositions and medicaments, are administered to the animal using a variety of administration routes. Such routes include oral, intranasal, intravenous, intramuscular, intragastric, transpyloric, subcutaneous, rectal, and the like. Preferably, the compounds and compositions are administered orally.

In another aspect, the invention provides methods for treating, reducing, or preventing deterioration of at least one component of the visual system of an animal. The methods comprise identifying an animal for which treating, reducing, or preventing deterioration of one or more components of the visual system of an animal is desired and administering in conjunction to the animal one or more UFA and one or more supplements that can be metabolized by the animal to produce nitric oxide releasing compounds (NORC) in an amount effective for treating, reducing, or preventing deterioration of one or more components of the visual system of an animal.

For such methods, the supplement is generally citrulline or ornithine, as arginine and most of its NORC derivatives do not require metabolism to produce a NORC compound. In one embodiment, the animal is a human, in another the animal is a canine or a feline companion animal. In various embodiments, the animal is an aged animal.

The UFA generally comprises one or more of ALA, EPA, DPA, DHA, or another n-3 fatty acid from any source, but a preferred UFA is from a fish oil source in certain embodiments.

In some embodiments, the UFA and supplement are administered together or separately in a composition. Generally, the composition comprises from about 0.1 to about 50% UFA, and in some embodiments, the UFA content is from about 0.5 to about 20%, from about 1 to about 15%, or from about 1 to 2 to about 5 to 10%. Similarly, the composition comprises from about 0.1 to about 20% supplement.

In various embodiments, the composition further comprises one or more B vitamins in an amount effective for treating, reducing, or preventing deterioration of at least one component of the visual system of an animal, such as from about 0.1 to about 40 times the recommended daily requirement of B vitamins.

In some embodiments, the composition further comprises one or more antioxidants in an amount effective for treating, reducing, or preventing deterioration of at least one component of the visual system of an animal, such as from about 0.0001 to about 25% of antioxidants.

In some embodiments, the composition comprises both antioxidants and one or more B vitamins in an amount effective for treating, reducing, or preventing deterioration of at least one component of the visual system of an animal. For example, the composition comprises from about 0.1 to about 40 times the recommended daily requirement of B vitamins and from about 0.0001 to about 25% of antioxidants in certain embodiments.

Methods in accordance with this aspect of the invention use such compositions as described above and throughout this disclosure, and are preferably useful where the deterioration of the visual system comprises deterioration of one or more of the retina, the optic nerve, or another component of the visual system.

In any such methods, the composition may be formulated as a human food composition, pet food composition, or a dietary supplement for some embodiments. In addition to the UFA and the NORC, the food composition further can comprise from about 15 to about 50% protein, from about 5 to about 40% fat, and from about 5 to about 20% moisture, and an ash content of from about 5 to about 10%.

The UFA and NORC are administered on an extended regular basis for some embodiments, and on a daily basis for one embodiment. Daily administration in accordance with the methods herein may be continued on an extended regular basis.

In one embodiment, the compounds or compositions are administered to the animal in conjunction with one or more therapeutic agents useful for, and in an amount effective for treating, reducing, or preventing deterioration of one or more components of the visual system of an animal.

Therapeutic agents for treating, reducing, or preventing deterioration of one or more components of the visual system of an animal include one or more of an Age-Related Eye Diseases Study (AREDS) vitamin formulation, a macular carotenoid, a VEGF or VEGF receptor inhibitory compound, an intravitreal steroid, a steroid analogue, a tyrosine kinase inhibitor, an anti-angiogenesis compound, or a protein kinase C inhibitor.

VEGF inhibitory compounds contemplated for use herein include aptamers, antibodies, RNAi compounds, receptor blockers, and tyrosine kinase inhibitors.

The therapeutic agent for treating, reducing, or preventing deterioration of one or more components of the visual system of an animal is preferably pegaptanib, verteporfin, bevacizumab, ranibizumab, VEGF Trap, anecortave acetate, squalamine, Sirna-027, Cand5, ganciclovir, ruboxistaurin mesylate, or hyaluronidase, or any combination thereof.

In one embodiment, the composition administered is a pharmaceutical or nutraceutical composition that optionally comprises one or more therapeutic agents useful for treating, reducing, or preventing the deterioration.

In another embodiment, the UFA and NORC are administered to the animal in conjunction with one or more physical treatments useful for treating, reducing, or preventing the deterioration of one or more of the retina, the optic nerve, or another component of the visual system. The physical treatments are one or more of rheotherapy, or photodynamic therapy, or the like.

In one embodiment, the treatment is administered further in conjunction with one or more therapeutic agents also useful for treating, reducing, or preventing the deterioration, because such treatments have not been proven to be effective as montherapies. The therapeutic agent is preferably one or more of an Age-Related Eye Diseases Study (AREDS) vitamin formulation, a macular carotenoid, a VEGF or VEGF receptor inhibitory compound, an intravitreal steroid, a steroid analogue, a tyrosine kinase inhibitor, an anti-angiogenesis compound, or a protein kinase C inhibitor.

For such methods to be most useful, the deterioration is age-related, disease-related, or injury-related. In one embodiment, the animal is an aged animal, preferably a healthy aging animal, and also preferably a companion animal. The animal in one embodiment has a phenotype associated with age-related deterioration of the visual system. In various embodiments, the phenotype includes one or more of: decreased rate of perception, acquisition, or processing of visual information; decreased ability to perceive, acquire, or process visual information independent of rate; decreased visual acuity, decreased visual discrimination, changed shape of an eyeball, changed refractive errors (e.g., presbyopia, myopia, hyperopia, astigmatism, etc.), increased presence of cataracts, floaters, and/or flashes; altered pupil size; altered photoreceptor number or function; altered perception of depth, color, and/or motion, altered contrast sensitivity, altered ability to distinguish light and dark; altered ability to locate, identify, or avoid objects; altered visual search ability; altered ability to distinguish figure from ground; altered ability to process visual information or perform tasks associated with visual input; altered problem-solving related to visual information; altered ability to recall visual information; altered ability to track an object or target; altered response times of the visual system or parts thereof, such as time to focus, pupillary response time to a stimulus, time to adjust to any new visual input (e.g., change in light or other input), time to process a visual input; altered blink rate, blink interval, and/or blink response time to a stimulus; each of the foregoing as compared to a control animal not having the phenotype.

In a further aspect, the invention provides methods for promoting the health and wellness of animals. The methods comprise identifying an animal susceptible to or suffering from deterioration of one or more components of the visual system and administering in conjunction to the animal one or more UFA and one or more nitric oxide releasing compounds (NORC) in an amount effective for treating, reducing, or preventing deterioration of such components of the visual system; thereby promoting the health and wellness of the animal. The preferred UFA and NORC are also described herein, e.g., ALA, EPA, DPA, DHA, and arginine.

In certain embodiments, the deterioration is age-related, disease-related, or injury-related. In various embodiments, the animal is a human or companion animal, preferably an adult animal, and more preferably an aging animal.

In various embodiments, the methods further comprise administering one or more B vitamins, one or more antioxidants, or combination thereof to the animal in an amount effective for treating, reducing, or preventing deterioration of at least one component of the visual system. Preferred amounts are described herein for other methods.

In another aspect, the invention provides methods for extending the prime years of life for animals. The methods comprise identifying an animal susceptible to or suffering from deterioration of one or more components of the visual system and administering to an animal in conjunction one or more UFA and one or more NORC in an amount effective for treating, reducing, or preventing deterioration of at least one component of the visual system of the animal, thereby extending the prime for the animal. The deterioration is age-related, disease-related, or injury-related. The preferred UFA and NORC are described herein, e.g., ALA, EPA, DPA, DHA, and arginine.

In certain embodiments, the deterioration is age-related, disease-related, or injury-related. In various embodiments, the animal is a human or companion animal, preferably an adult animal, and more preferably an aging animal.

In various embodiments, the methods further comprise administering one or more B vitamins, one or more antioxidants, or combination thereof to the animal in an amount effective for treating, reducing, or preventing deterioration of at least one component of the visual system. Preferred amounts are described herein for other methods.

In another aspect, the invention provides methods for improving the quality of life of animals. The methods comprise identifying an animal susceptible to or suffering from deterioration of one or more components of the visual system and administering one or more UFA and one or more NORC to the animal in an amount effective for treating, reducing, or preventing deterioration of at least one component of the visual system of an animal, thereby improving the quality of life of the animal. The preferred UFA and NORC are also described herein, e.g., ALA, EPA, DPA, DHA, and arginine.

In one embodiment, the deterioration is preferably age-related, disease-related, or injury-related. In another, the animal is a human or companion animal, preferably a juvenile or adult animal, and more preferably an aging animal.

In various embodiments, the methods further comprise administering one or more B vitamins, one or more antioxidants, or combination thereof to the animal in an amount effective for treating, reducing, or preventing deterioration of at least one component of the visual system. Preferred amounts are described herein for other methods.

In another aspect, the invention provides a package useful for containing one or more UFA, NORC, B vitamins, antioxidants, or other components of the invention and an indication that the package contains compounds that are effective for treating, reducing, or preventing deterioration of one or more components of the visual system of an animal. The package comprises at least one material suitable for containing the components and a label affixed to the material containing a word or words, picture, design, acronym, slogan, phrase, or other device, or combination thereof, that indicates that the package contains the components and indicates their use. Typically, such device comprises the words "improves vision" or "contains ingredients that treat, reduce, or prevent deterioration of the visual system" or an equivalent expression printed on the material. Any package configuration and packaging material suitable for containing the components are useful in the invention, e.g., a bag, box, bottle, can, pouch, and the like manufactured from paper, plastic, foil, metal, and the like. In preferred embodiments, the package further comprises UFA, NORC, B vitamins, antioxidants, or other components of the invention. In various embodiments, the package further comprises at least one window that permit the package contents to be viewed without opening the package. In some embodiments, the window is a transparent portion of the packaging material. In others, the window is a missing portion of the packaging material.

The compounds and compositions useful in the methods of the invention, including the pharmaceutical compositions and medicaments, are administered to the animal for a time required to accomplish one or more objectives of the invention, e.g., treating, reducing, or preventing deterioration of a component of the visual system in the animal, particularly the retina, the optic nerve and other components of the visual system; and/or altering at least one phenotype exhibited by an animal experiencing deterioration of a component of the visual system. The compositions are suitable for long-term administration or administration on any schedule compatible with the composition and objective.

EXAMPLES

The invention can be further illustrated by the following examples, although it will be understood that the examples are included merely for purposes of illustration and are not intended to limit the scope of the invention unless otherwise specifically indicated.

Example 1

Test Compositions and Animal Groups

Young adult (2 to 3 months old) female Charles River rats were ovariectomized (OVX) and fed one of 5 compositions for 4 weeks or treated with estradiol (E2) as a positive control for one week. The animal groups and respective compositions were:

| Composition No. | Composition |
| --- | --- |
| 1 | Fish oil + Arginine + B vitamins + Antioxidants (AOX) (15 rats for lesions volume and apoptosis) |
| 2 | Fish oil + Arginine + B vitamins (15 rats for lesions volume and apoptosis) |
| 3 | Fish oil + Arginine + AOX (15 rats for lesions volume and apoptosis) |
| 4 | Fish oil + Arginine (15 rats for lesions volume and apoptosis) |
| 5 | E2 (15 rats for lesions volume and apoptosis) |
| 6 | Control (15 rats for lesions volume and apoptosis) |

The Control was a standard rat diet containing 140 g/kg casein, 100 g/kg sucrose, 50 g/kg fiber, 155 g/kg dextrin, 466 g/kg corn starch, 35 g/kg standard salt mix, 40 g/kg soybean oil, 10 g/kg standard vitamin mix, 1.8 g/kg L-cystine and 2.5 g/kg choline chloride. Composition 1 was the Control plus 2% Arginine, and 2% Menhaden fish oil, 4× B vitamins, and antioxidants (Vitamin E: 500 mg/kg diet, Vitamin C: 150 mg/kg diet, Astaxanthin:100 mg/kg, selenium: 0.40 mg/kg). Composition 2 was the Control plus 2% Arginine, and 2% Menhaden fish oil, and 4× B vitamins. Composition 3 was the Control Diet plus 2% Arginine, and 2% Menhaden fish oil, and antioxidants (Vitamin E: 500 mg/kg diet, Vitamin C: 150 mg/kg diet, Astaxanthin:100 mg/kg, selenium: 0.40 mg/kg). Composition 4 was the Control plus 2% Arginine, and 2% Menhaden fish oil.

At the end of the 4 weeks of feeding (or 1 week of E2 treatment), the animals were subjected to a transient (1 hour) middle cerebral artery occlusion followed by reperfusion for 24 hours to mimic one of the main causes of neuron loss. Then, the animals were euthanized for determination of brain lesion volume and subsequent terminal deoxynucleotidyl transferase dUTP nick end labeling (TUNEL) staining to evaluate apoptosis in and around brain lesions.

Example 2

TTC Staining and Neuron Loss Determination

The brains of the rats from Example 1 were removed immediately after euthanization, dissected coronally into 2 mm sections using a metallic brain matrix (ASI Instruments, Inc., Warren, Mich.), and stained by incubation in a 2% 2,3, 5-Triphenyl-2H-tetrazolium chloride (TTC) in a 0.9% saline solution at 37° C. for 30 min. Photographs were taken with a digital camera. The digital images of each brain section were used to calculate lesion volume for the infracted area of the brain.

Example 3

TUNEL Staining and Cell Death Quantification

TUNEL staining was conducted on the same tissue used for assessment of lesion volume in Example 2. Brain slices were post-fixed in 4% formalin for later sectioning for subsequent staining for TUNEL positive neurons. DNA fragmentation was detected by a TUNEL method using a Dead END fluorescent kit (Promega, Madison, Wis.) according to the manufacturer's instruction. Colocalization with TUNEL staining with other antigens was achieved by confocal microscopy, with Alexa-Fluorophore conjugated secondary antibodies that do not overlap with FITC-labeled TUNEL stain.

Cell counting was performed in the ischemic boundary cortex under a CAST-Grid system (Nikon, Inc). The region was delineated in the ischemic brain cortex near the edge of the surface, where the highest density of TUNEL-positive cells was observed. Within these boundaries, optical dissectors were systematically randomly sampled and the number of positive cells, together with DAPI labeled nuclear counterstain in each optical section is counted. The positive labeled cell numbers in the investigated region were normalized with the total number of cells, indicated by DAPI stain. The data were expressed as the percentage of DAPI nuclear counterstained cells. The results are shown in Table 1 and Table 2.

TABLE 1

TUNEL Staining

| Group | N | Value |
|---|---|---|
| 17β-Estradiol | 14 | 37.69 |
| Control | 14 | 71.77 |
| Fish Oil + Arg | 14 | 53.10 |
| Fish Oil + Arg + AOX | 14 | 44.04 |
| Fish Oil + Arg + VitB | 14 | 44.10 |
| Fish Oil + Arg + VitB + AOX | 14 | 45.01 |

TABLE 2

Lesion Volume

| Group | N | Value |
|---|---|---|
| 17β-Estradiol | 14 | 147.41 |
| Control | 14 | 286.00 |
| Fish Oil + Arg | 14 | 194.86 |
| Fish Oil + Arg + AOX | 14 | 167.51 |
| Fish Oil + Arg + VitB | 14 | 167.79 |
| Fish Oil + Arg + VitB + AOX | 14 | 171.32 |

Referring to Table 1 and Table 2, the data show that the animals receiving the diets containing the UFA and NORC had substantially smaller lesions with substantially less cell death associated with those smaller lesions. All groups receiving fish oil (UFA) and arginine (NORC) had better outcomes than the control group. Additional benefits were observed by including either or both of antioxidants and B vitamins in the diet.

Example 4

Rat Experiments

The experimental design of Example 1 is used. Five groups of rats are used and are fed different diets as in Example 1. The rats are aging rats that have lived at least 50-75% of their average life expectancy. The rats are fed their respective daily diet containing UFA, NORC, and optionally B vitamins and/or antioxidants for a prolonged period ("extended regular basis"). The rats are exposed to a pulse of light of varying intensity and duration and pupillary response is measured. The experiment is conducted such that only one eye is pulsed and the response of the pulsed eye can be compared to the unpulsed eye for each rat. The pupillary responses for rats in the groups receiving the UFA/NORC diets are measured and compared to the control group not receiving the UFA and NORC diet. The results will show substantially better performance among the rats receiving the protective diets compared to those of the control group.

An experimental model of retinal detachment induced in rats by injecting hyaluronic acid into the subretinal space is tested in the rats at the conclusion of the feeding experiments for pupillary response. Such a model tests the protective effect of UFA and NORC on injury-induced deterioration of the visual system. The test should show that the rats fed UFA/NORC containing diets will suffer less extensive detachment and less apoptosis in the affected area than the control group. (See e.g., Vision Research 33(4):437-446 (March 1993); See also, Invest. Ophthalmol. Vis. Sci. 44(3): 1262-1267 (March 2003).

Example 5

Dog Experiments

Aging dogs are used and divided into groups receiving either a control diet (complete) or a diet with added UFA, NORC, and optionally, B-vitamins and/or antioxidants.

The dogs are maintained on the diets for an extended period and then challenged with several tests related to visual deterioration. Pupil light reflexes are measured following a pulse of light in a fashion similar but not identical to Example 4. The pupil light reflex (PLR) is an objective parameter of retinal and optic nerve function. Both transient and sustained responses are measured. Responses from the dogs receiving the diets with additional UFA and NORC should be substantially improved relative to those from the dogs fed the control diet.

Additional tests, such as visual memory of objects or tracking motion of an object can be scored for dogs receiving different diets. Results should show that the dogs receiving the UFA/NORC diets have better responses to these challenges. See e.g., Invest. Ophthalmol. Vis. Sci. 48(11): 5178-5183 (November 2007).

Example 6

Experiments similar to those performed in Example 5 are performed using dogs having a genetic propensity for retinal disorders.

The results from the Examples show that the compounds of the invention are useful for treating, reducing, or preventing deterioration of one or more components of an animal's visual system.

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for treating, reducing, or preventing deterioration of one or more components of the visual system of an animal comprising identifying an animal susceptible to or suffering from deterioration of one or more components of the visual system and administering in conjunction to the animal one or more unsaturated fatty acids (UFA) and one or more nitric oxide releasing compounds (NORC) in an amount effective for treating, reducing, or preventing deterioration of such components of the visual system.

2. The method of claim 1 wherein deterioration comprises deterioration of one or more of the retina, the optic nerve, or another component of the visual system.

3. The method of claim of claim 2 wherein the deterioration comprises deterioration of one or more of the retinal pigment epithelium, the outer segment (photoreceptors), the inner segment (photoreceptors), the outer limiting membrane, the outer nuclear layer, the outer plexiform layer, the inner nuclear layer, the inner plexiform layer, the ganglion cell layer, the nerve fiber layer, or the inner limiting membrane.

4. The method of claim 2 wherein the another component of the visual system comprises one or more of the optic chiasm, the optic tract, the lateral geniculate nucleus (LGN) and/or related tissues of the thalamus, the superior colliculus, the optic radiation, the primary visual cortex of the brain (V1), the prestriate cortex (V2), the third visual complex, visual area V4, visual area V5, the pretectal nucleus, or the superchiasmatic nucleus.

5. The method of claim 1 wherein the deterioration is caused by normal aging in the absence of an injury or disease identifiable as a substantial source of the deterioration.

6. The method of claim 1 wherein the deterioration is caused by injury.

7. The method of claim 6 wherein the injury is an age-related injury.

8. The method of claim 6 wherein the injury is a retinal tear, a macular hole, an epiretinal membrane, or a retinal detachment.

9. The method of claim 1 wherein the deterioration is caused by disease.

10. The method of claim 9 wherein the disease is an age-related disease.

11. The method of claim 9 wherein the disease is retinitis, optic neuritis, macular degeneration, proliferative or nonproliferative diabetic retinopathy, diabetic macular edema, progressive retinal atrophy, progressive retinal degeneration, sudden acquired retinal degeneration, immune-mediated retinopathy, retinal dysplasia, chorioretinitis, retinal ischemia, retinal hemorrhage, hypertensive retinopathy, retinal inflammation, retinal edema, retinoblastoma, or retinitis pigmentosa.

12. The method of claim 1 wherein the animal is a human or a companion animal.

13. The method of claim 1 wherein the UFA comprises one or more of ALA, EPA, DPA, DHA, or another n-3 fatty acid from any source.

14. The method of claim 1 wherein the UFA are from a fish oil source.

15. The method of claim 1 wherein the NORC are arginine, a nitric oxide-releasing analog or derivative or arginine, citrulline, or ornithine.

16. The method of claim 1 wherein the UFA and the NORC are administered to the animal in amounts of from about 0.001 g/kg to about 50 g/kg.

17. The method of claim 1 wherein the UFA and the NORC are administered to the animal daily.

18. The method of claim 1 further comprising administering in conjunction to the animal one or more B vitamins in an amount effective for treating, reducing, or preventing the deterioration.

19. The method of claim 18 wherein the B vitamins are administered in an amount of from about 0.1 to about 40 times the recommended daily requirement of B vitamins.

20. The method of claim 1 further comprising administering in conjunction to the animal one or more antioxidants in an amount effective for treating, reducing, or preventing the deterioration.

21. The method of claim 20 wherein the antioxidants are administered in an amount of from about 0.1 to about 10 times the recommended daily allowance for the antioxidants.

22. The method of claim 20 wherein the antioxidants include one or more of Vitamin C, Vitamin E, a tocopherol or tocotrienol compound with Vitamin E activity, zeaxanthin, astaxanthin, lutein, or selenium.

23. The method of claim 1 further comprising administering in conjunction to the animal one or more B vitamins and one or more antioxidants in an amount effective for treating, reducing, or preventing deterioration.

24. The method of claim 23 wherein the B vitamins are administered in an amount of from about 0.1 to about 40 times the recommended daily requirement of B vitamins and the antioxidants are administered in an amount of from about 0.1 to about 10 times the recommended daily allowance for the antioxidants.

25. The method of claim 1 wherein the UFA and NORC are administered as part of a composition formulated as a human food composition, a pet food composition, or a dietary supplement.

* * * * *